United States Patent [19]
Keller et al.

[11] Patent Number: 6,015,599
[45] Date of Patent: *Jan. 18, 2000

[54] HIGH VERTICAL ASPECT RATIO THIN FILM STRUCTURES

[75] Inventors: Christopher G. Keller, Albany; Mauro Ferrari, Walnut Creek, both of Calif.

[73] Assignee: Regents of the University of California, Berkeley, Calif.

[ * ] Notice: This patent is subject to a terminal disclaimer.

[21] Appl. No.: 08/479,669

[22] Filed: Jun. 6, 1995

Related U.S. Application Data

[62] Division of application No. 08/207,459, Mar. 7, 1994, Pat. No. 5,660,680.

[51] Int. Cl.[7] ........................................................ B32B 3/12
[52] U.S. Cl. .......................... 428/34.4; 428/116; 428/167; 428/188; 251/14; 200/329
[58] Field of Search ..................................... 428/116, 34.4, 428/163, 167, 188; 251/14; 200/329

[56] References Cited

U.S. PATENT DOCUMENTS

5,645,684  7/1997  Keller .................................... 156/643.1

*Primary Examiner*—Timothy M. Speer
*Attorney, Agent, or Firm*—William J. Egan, III; Fish & Richardson P.C.

[57] ABSTRACT

This invention relates to the area of microelectromechanical systems in which electronic circuits and mechanical devices are integrated on the same silicon chip. The method taught herein allows the fabrication of thin film structures in excess of 150 microns in height using thin film deposition processes. Wafers may be employed as reusable molds for efficient production of such structures.

14 Claims, 12 Drawing Sheets

HIGH VERTICAL ASPECT RATIO THIN FILM STRUCTURES

This is a divisional of application Ser. No. 08/207,459 filed Mar. 7, 1994 now U.S. Pat. No. 5,660,680.

BACKGROUND OF THE INVENTION

The present invention relates generally to micromachined structures, and more particularly to three-dimensional, thin-film, micromachined structures.

Microelectromechanical systems (MEMS) integrate micromechanical and microelectronic devices on the same silicon chip. These systems have many useful applications such as microsensors and microactuators. The accelerometer chips used to trigger air bag inflation in automobiles in the event of a collision are an example of a microsensor. Microvalves used to control fluidic circuits are an example of microactuators.

Microstructures are made by photolithography and etching of deposited thin films to yield a desired shape. This is called "surface micromachining" because the thin films can only be deposited on a surface. This limits the height of the structure to approximately the thickness of the film. The films are typically formed through the process of chemical vapor deposition (CVD).

Typically, a layer of silicon dioxide is used wherever a sacrificial material is needed. The final step of fabrication is to etch away this material to open up passageways, or clearances between moving parts of the microstructure. Sacrificial layers are needed during processing to prevent structural layers from being deposited directly in contact with already-deposited structural layers, except in locations where interlayer contact and bonding is desired. Since the resulting structures have microscopic thicknesses, they can only withstand microscopic forces without breaking. There has long been a need for a way to make milli-scale structures (structures with dimensions on the order of 100 microns) of any arbitrary shape required. For example, tubing manifolds and enclosed vessels that may be used in fluidic systems such as in the field of microscale chemical processing with liquid or gaseous reagents.

There are methods for making milli-scale structures by chemical etching of silicon wafers, but these are restricted to certain crystal planes and cannot be used to make any arbitrary shape that may be required.

Accordingly, an object of the present invention is to provide free-standing, high-vertical aspect ratio thin film structures.

Another object of the present invention is to provide high-vertical aspect ratio thin film structures integrated with planar electronic circuits.

Yet another aspect of the present invention is to provide free-standing, hollow thin film structures.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the claims.

SUMMARY OF THE INVENTION

The present invention is directed to a free-standing thin film structure whose extent in any direction is greater than about twice the thickness of its thin films. A free-standing structure is a structure not attached to a substrate.

Such substrates are made possible by the fabrication methods of the present invention. These methods include the steps of providing a mold, coating the mold with a sacrificial thin film layer, and growing a thin film on the sacrificial thin film layer, with the thickness of the thin film being less than the highest depth of the mold. The sacrificial thin film layer is then etched to obtain a free standing thin film structure.

Such structures allow fabrication of fluidic devices and micromechanical systems of greater dimensions than can be achieved using planar thin-films.

BRIEF DESCRIPTION OF THE DRAWINGS

The accompanying drawings, which are incorporated in and constitute a part of the specification, schematically illustrate a preferred embodiment of the invention and, together with the general description given above and the detailed description of the preferred embodiment given below, serve to explain the principles of the invention.

DESCRIPTION OF THE PREFERRED EMBODIMENT

Figure 1:
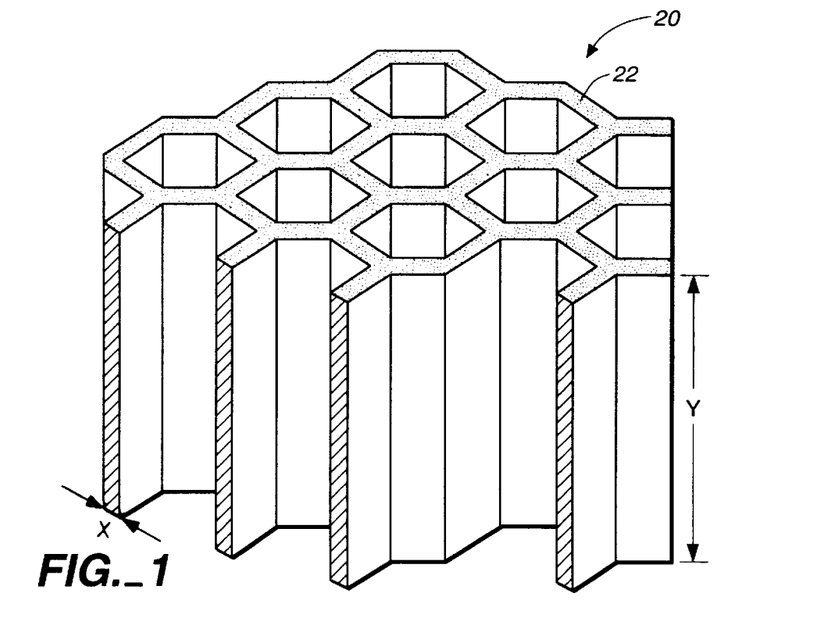
FIG. 1 is a schematic, perspective view of a portion of a high-vertical aspect ratio microelectromechanical structure (HARMEMS) according to the present invention.

The present invention will be described in terms of several preferred embodiments. The preferred embodiments are high vertical aspect ration thin film structures or high vertical aspect ratio microelectromechanical structures (HARMEMS) and methods for their fabrication. A portion 20 of such a structure is shown in FIG. 1.

Structure 20 is a honeycomb-shaped network of thin film beams or ribs 22. The thin films forming beams or ribs 22 are oriented in a vertical plane. The vertical extent of structure 20, represented by dimension y, may be in the range of about 5 microns to about 250 microns, with the preferred value being determined by the forces that will be applied to the structure in use, much larger than the thickness of beams 22 represented by dimension x, which may typically be in the range of about 5 microns to about 15 microns. Structure 20 is light-weight, and its mechanical strength is much larger than that of a planar thin film. Since the bending stiffness increases with the cube of the thickness, a 100 micron thick honeycomb is about 125,000 stiffer than the typical 2 micron beams made in the art of surface silicon today. Structure 22 is free-standing and its extent in any direction is greater than twice the thickness of the thin film forming beams 22.

Figure 2:
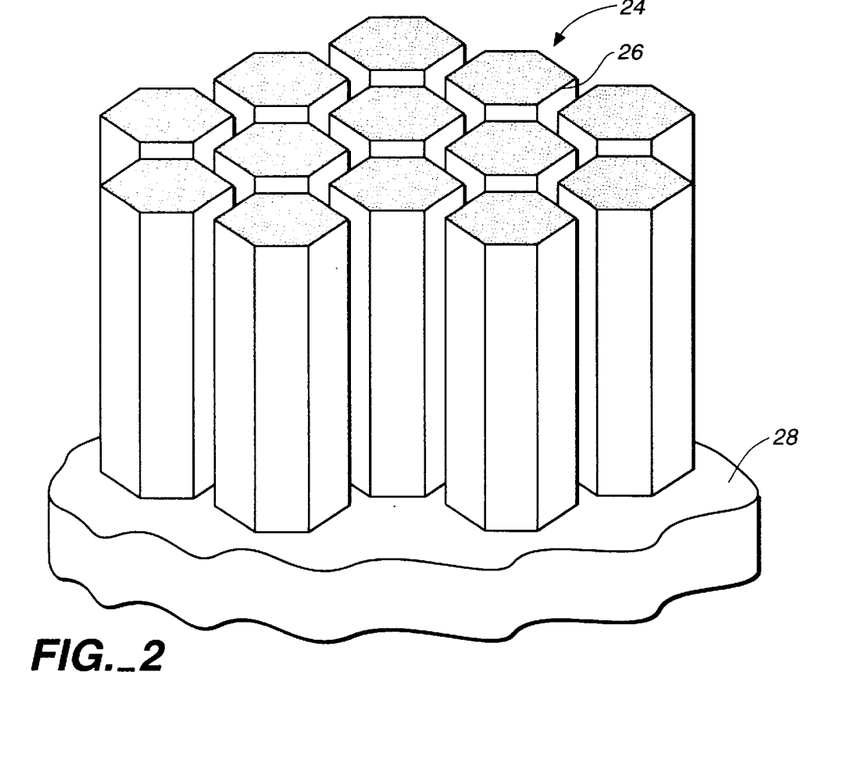
FIG. 2 is a schematic, perspective view of a portion of a mold used to fabricate the structure of FIG. 1.

Structure 20 may be fabricated using mold 24 of FIG. 2. Mold 24 may be formed by anisotropically etching photolithographically patterned vertical trenches 26 in a substrate such as a silicon wafer. The depth of trenches 26 is equal to the desired vertical extent of the HARMEMS 20 to be fabricated. Trenches 26 do not extend all the way through the wafer, leaving an unetched silicon base 28.

To form a silicon mold, a silicon wafer may be coated with sufficient silicon dioxide to serve as a mask for the required trench etch depth. Silicon dioxide is a good material to use as a mask for etching silicon because it holds up for a relatively long time under the conditions of the silicon etch process. The silicon dioxide may be grown by thermal oxidation of the silicon wafer or by chemical vapor deposition (CVD). The silicon dioxide is coated with photoresist. The photoresist is exposed to a mask which has the desired layout for the HARMEMS. The photoresist is then developed and hardbaked. The pattern is etched to expose the silicon in the areas where the trenches are to be etched. The etch may be done by well known methods, such as wet etching using hydrofluoric acid (HF) or more preferably the oxide mask is etched anisotropically by plasma so that vertical sidewalks are left in the oxide and no significant lateral etching occurs.

The trenches are then etched anisotropically into the depth of the silicon using plasma etching. The parameters for this process may be 180 sccm chlorine, 400 sccm Helium, 300 Watts, 425 millitorr and 0.8 cm gap. The etching plasma is prevented from contacting the silicon that lies under the oxide. This etch step must be terminated before the oxide mask is completely consumed. Typically, the thickness of the oxide decreases by 1 micron during the etching of 20 microns of silicon.

Figure 3A:
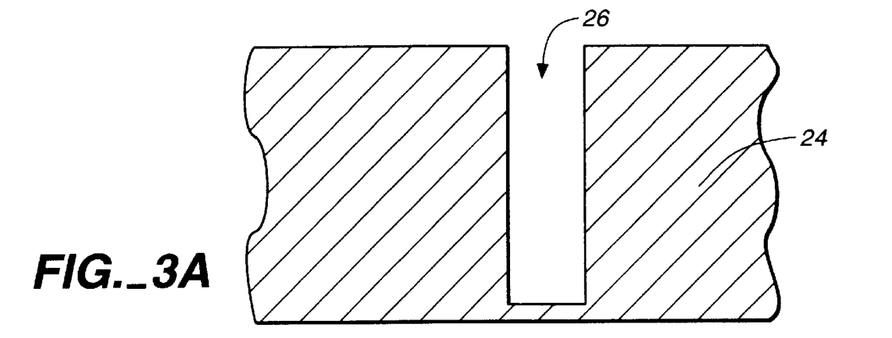
FIGS. 3A–3D are schematic, cross-sectional views of stages in the fabrication of a HARMEMS.

The etched surface of the wafer may be made smoother if desired by growing 1 micron of thermal oxide on it and then etching this oxide away with a solution of 49% hydrofluoric acid (HF). One micron of undoped CVD silicon dioxide (undoped means pure silicon dioxide in this case) may then be deposited. This material is called low temperature oxide (LTO). A cross sectional view of a resulting trench 26 is shown in FIG. 3A. At this point a mold such as mold 24 of FIG. 2 has been obtained.

Figure 3B:
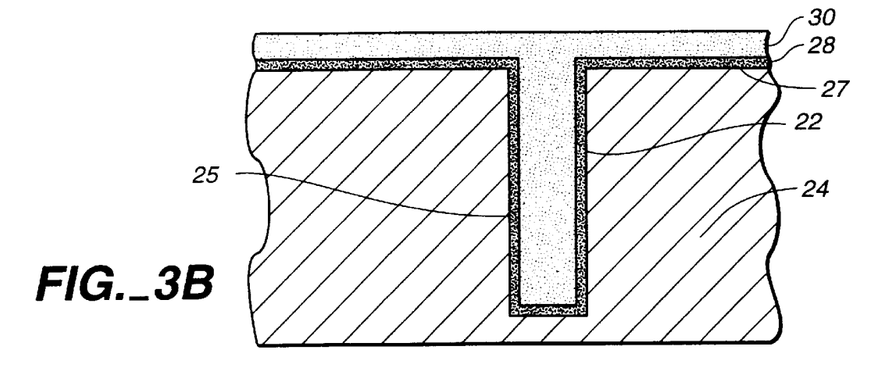

A sacrificial layer 28 is then deposited (FIG. 3B). This layer may consist of up to about four microns of phosphosilicate glass (PSG), that has a high etch rate in HF to facilitate the final removal of the HARMEMS from its mold. The coated mold may be annealed to densify and reflow the PSG to provide a smooth surface. The LTO layer prevents the diffusion of phosphorus into the silicon wafer.

Figure 3C:
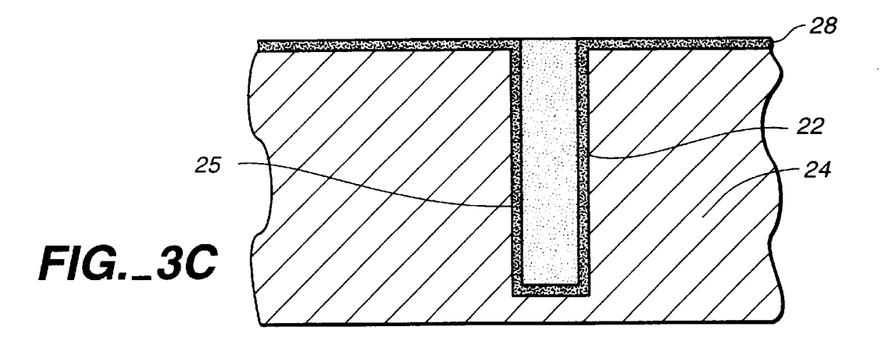

The remaining trench volume is then filled with CVD polysilicon 25. To ensure that the trench is completely filled, the deposition may be done at low temperature such as 580° C. When the trench is completely filled, the structure of FIG. 3B is obtained. Trench 26 and the top surface 27 of mold 24 are coated with a sacrificial layer 28. The remaining trench volume is filled with silicon, forming a beam 22. The thickness of the polysilicon thin film forming beam 22 is less than the depth of mold 24. A layer 30 of polysilicon also covers the mold. Layer 30 was formed at the same time layer 25 was formed. For some applications, such as a reinforced particle filter disclosed in copending application "Microfabricated Particle Filter" filed concurrent with the subject application and assigned to the assignee of the subject application, top layer 30 may be retained as part of the finished device, in which case it may now be patterned photolithographically. If a flat planar surface is desired, the wafer may be lapped and polished, removing part or all of layer 30, as shown by FIG. 3C. The wafer may now be annealed to relieve the internal stresses in the polysilicon, and to diffuse phosphorus from the PSG into the polysilicon to make it conductive. If nonconductive polysilicon is needed, the PSG can be coated with undoped LTO prior to the polysilicon deposition.

Figure 3D:
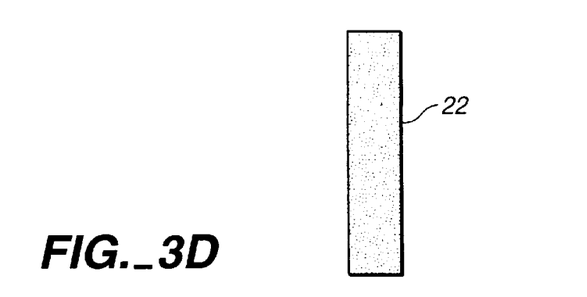

HARMEMS may then be released from the wafer by etching away the sacrificial oxide layer. Beam 22 of FIG. 3D is thus produced.

Surface micromachined microstructures may be built on top of the HARMEMS while it is still held in its mold.

If the trench etching was done under conditions that cause undercutting of the wafer, then hollow beams can be made. These may be used to conduct fluids, or cause movement in response to hydrostatic pressure. Other methods for fabricating hollow structures will be described below.

Figure 4:
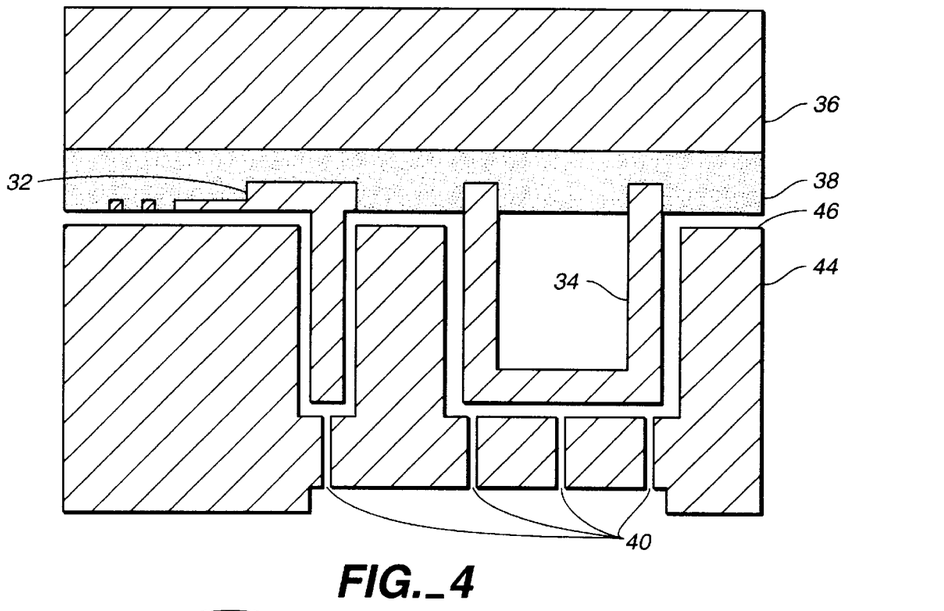
FIG. 4 is a schematic, cross-sectional view illustrating the extraction of HARMEMS from its mold.

FIG. 4 shows the removal of HARMEMS 32 and 34 from their mold 44, after the sacrificial layers coating the mold have been etched. If the wafer was lapped and polished before etching of the sacrificial layers, the HARMEMS extend beyond the top surface 46 of the mold, as shown. A flat wafer 36 with a sticky surface such as a coating of wax 38 may be used to lift structures 32 and 34 from the mold.

If mold 44 is n-type silicon, long small diameter passageways 40 leading to the mold cavities may be photoelectrochemically etched from the back and through the thickness of the mold. Possible process parameters for the electrochemical etching are 10 mA/cm$^2$ etching current, 10% HF concentration, platinum cathode, and light being shined on the back of the wafer i.e. the side opposite the trench patterned side. This technique may be used to connect the bottoms of the mold cavities to a source of hydraulic pressure. The preferred working fluid is deionized water with 0.1% surfactant such as Triton-X100, available from Sigma Chemical Co., 3500 De Kalb, St. Louis, Mo. 63118. To retain the organization of the parts fabricated in mold 44 in accordance with the present invention, the parts can be ejected directly into receiving cavities that have been etched into a second wafer (not shown).

The machines that can be built with the structures of the present invention typically consist of rigid beams connected by flexible links. Rigid structures can be made from thin films by using the thin films to construct a honeycomb structure like the one shown in FIG. 1. The outside perimeter of the honeycomb region, referred generally by reference numeral 55 (FIGS. 5A and 5B), is made in the shape of any desired machine part. This yields a rigid three-dimensional machine part that consists entirely of a relatively thin deposited films. The flexible connecting links in such a structure may be simple single bars of polysilicon, such as links 52 and 58 in FIGS. 5A and 5B.

Figure 5A:
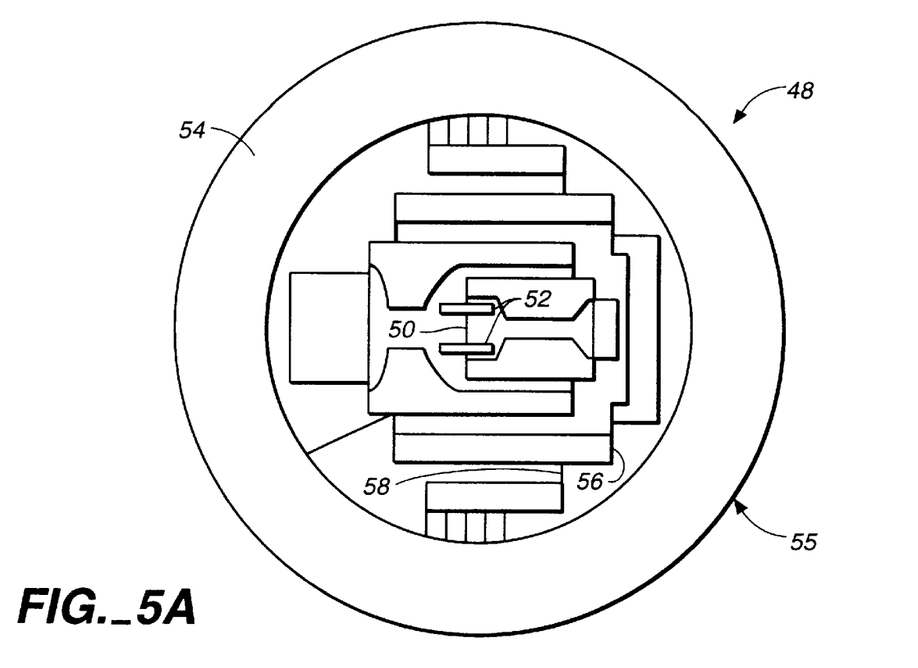
FIGS. 5A–5B are schematic, plan views illustrating the operation of a micro tensile testing machine formed as a HARMEMS.
Figure 5B:
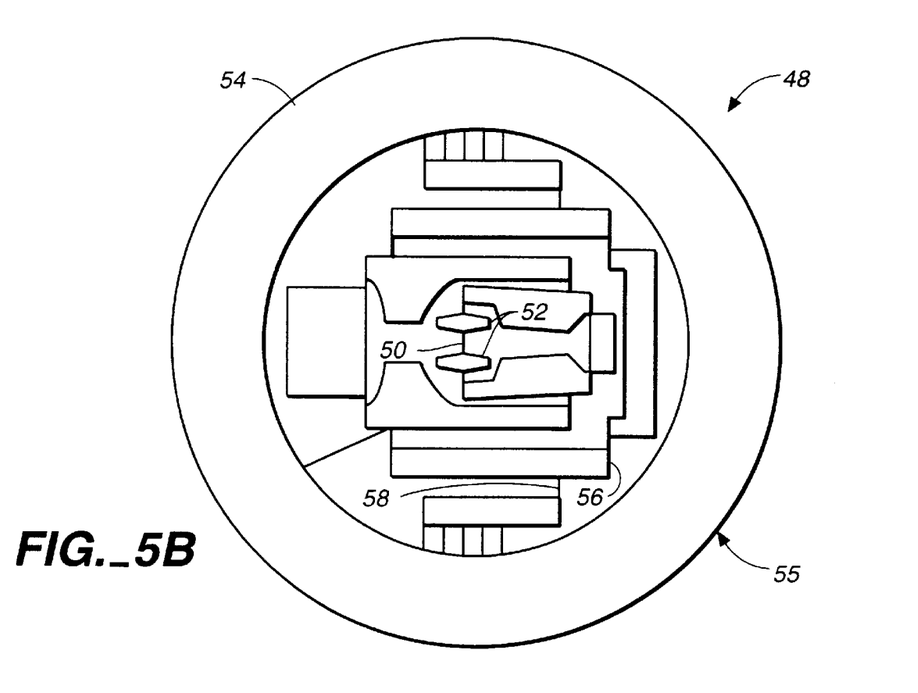

The layout of a microtensile testing machine 48 fabricated as described above is shown in FIGS. 5A and 5B. In these figures, circular frame 54 and member 56 are actually honeycomb structures like that of FIG. 1 whose details are too small to show. The thin lines illustrated in these figures are flexible thin film connecting links, such as link 58 and spring 52. To tension test structure 50, and electric current is passed through frame 54, which as a result heats up and expands. FIG. 5A shows machine 48 at a uniform temperature. In FIG. 5B, frame 54 is at a higher temperature than the rest of the machine. As a result, link 50 is subjected to tensile stress.

Figure 6A:
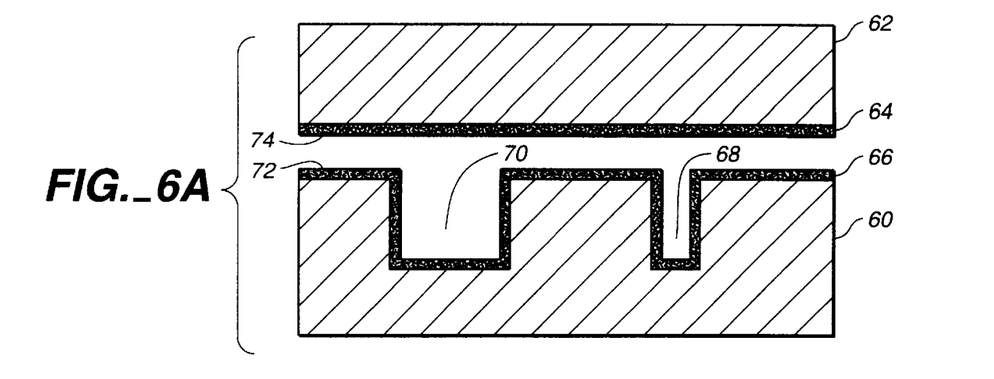
FIGS. 6A–6C are schematic, cross-sectional views illustrating the fabrication of a tubing manifold and a solid HARMEMS.
Figure 6B:
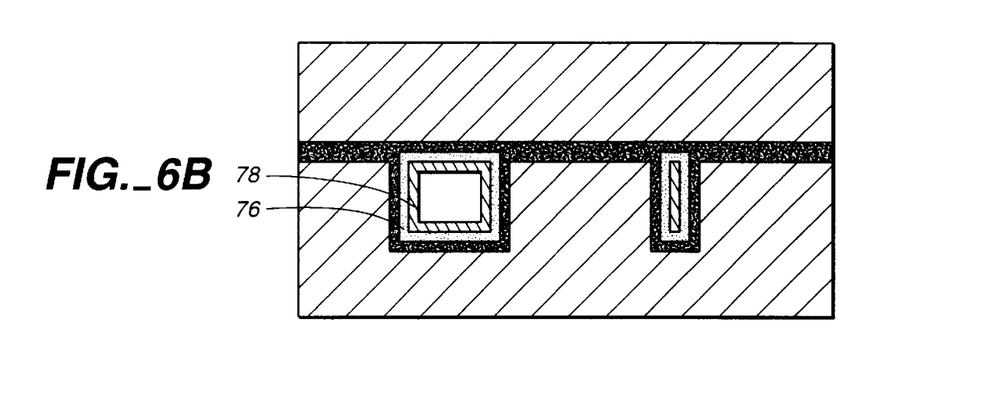

Tubing manifolds may be fabricated by using two wafers to form a mold, such as silicon wafers 60 and 62 of FIG. 6A. Tubing manifolds may be used for controlling fluid flow for microscale chemical reactions. Wafer 60 has mold cavities 68 and 70 etched into it as described above. Wafer 62 is flat. The two wafers are bonded together by anodic bonding, or hydrophilic thermal bonding. For this to work, the contacting surfaces 72 and 74 of the wafers (FIG. 6A) must be extremely flat to ensure a large area of contact. There must be a thin layer of silicon dioxide such as layers 64 and 66, or other easily etchable material, separating the silicon so that the wafer assembly can be taken apart later. Layers 64 and 66 are preferably thermal oxide on the order of 0.5 microns thick. After the wafers are bonded together, a sacrificial layer 76 (FIG. 6B) of PSG is deposited. As discussed, this is a high-etch rate material. If there are any voids left between the bonded wafers where they should be in contact, but where, because of surface imperfections or particle contamination they are not in contact, the PSG will fill such voids as well as line mold cavities 68 and 70. PSG layer 76 may be 1 to 10 microns thick. The PSG is annealed to densify it. This step may be carried out for one hour at 1050° C. A structural layer 78 of low pressure chemical vapor deposition (LPCVD) polysilicon is deposited and then annealed to relieve internal stresses. Structural layer 78 forms the finished parts 80 and 82. The structural layer may be 1 to 3 microns thick, and be annealed for one hour at 1000° C. Thicker polysilicon films can be built up if a stress relief anneal is done after the accumulation of each additional 3 microns of polysilicon. Other CVD films can be used instead of polysilicon. For example, silicon nitride parts can be made.

After the polysilicon deposition and anneal are complete, the polysilicon that has accumulated on the outside of the wafers much be removed to allow the sacrificial oxide layers 76 to be etched. Photoresist is first applied to the wafer to protect the polysilicon at the entry ports to the mold cavities. Small entry ports are simply plugged by photoresist, and in the case of wide entry ports, the photoresist may flow into the mold cavity. There must be no passageway for the etching plasma to strike the polysilicon parts, only the polysilicon film on the exterior of the wafers.

Once the polysilicon has been removed from the outside of the wafer assembly, the sacrificial oxide is exposed and can be etched by HF. An HF solution may be used to etch all of the oxide and PSG since it is a continuous film, even though it has complicated contours due to the presence of the mold cavities. The polysilicon is not etched by HF. It is preferred to cover the etching chamber with an opaque layer (such as aluminum foil) because photons can cause n-type silicon to etch.

Figure 6C:
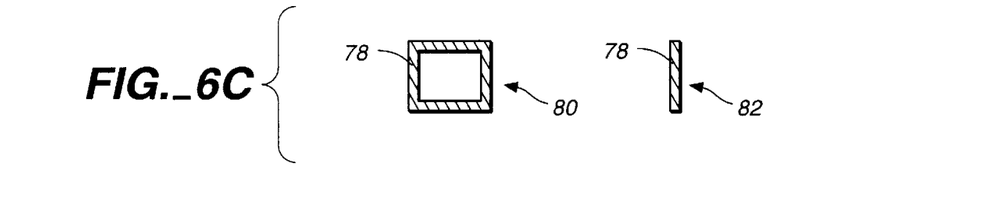

One the sacrificial material is dissolved, the wafers can be separated and the parts can be removed. The finished parts 80 and 82 are shown in FIG. 6C.

Figure 7A:
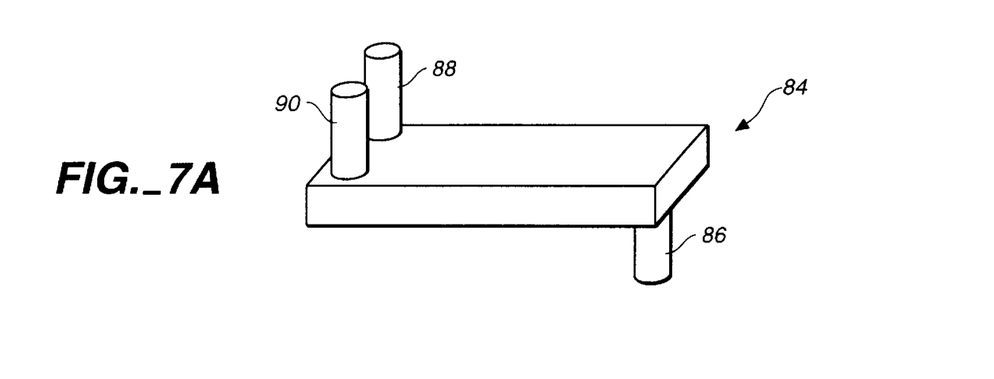
FIG. 7A is a schematic, perspective view of an enclosed vessel with ports according to the present invention.
Figure 7B:
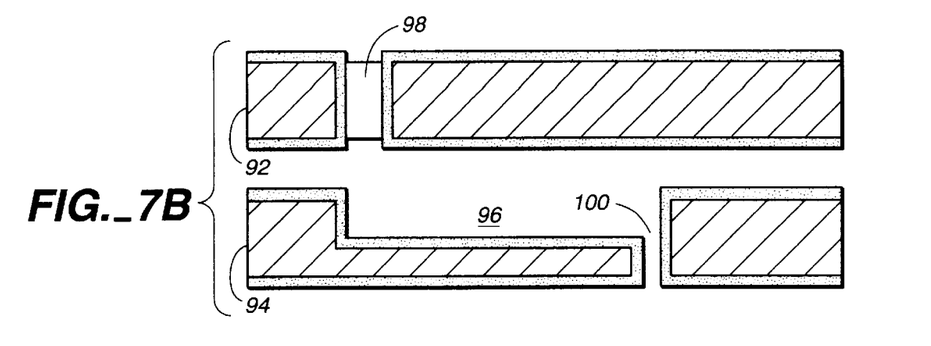
FIGS. 7B–7E are schematic, cross-sectional views illustrating the fabrication of the enclosed vessel of FIG. 7A.
Figure 7C:
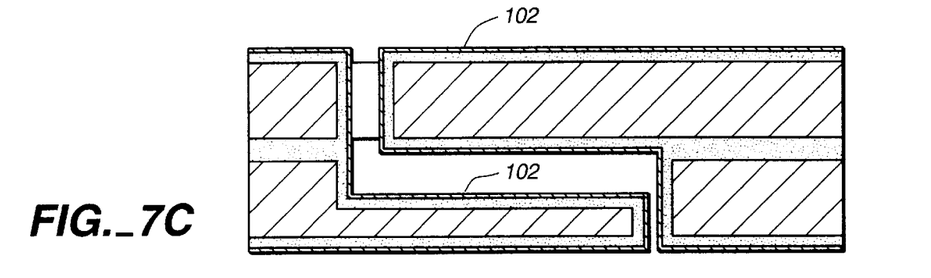
Figure 7D:
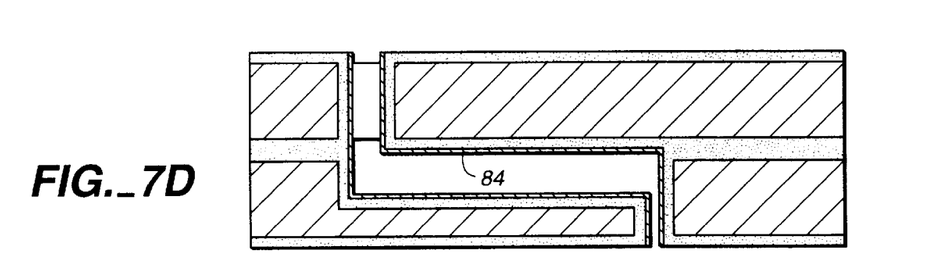
Figure 7E:
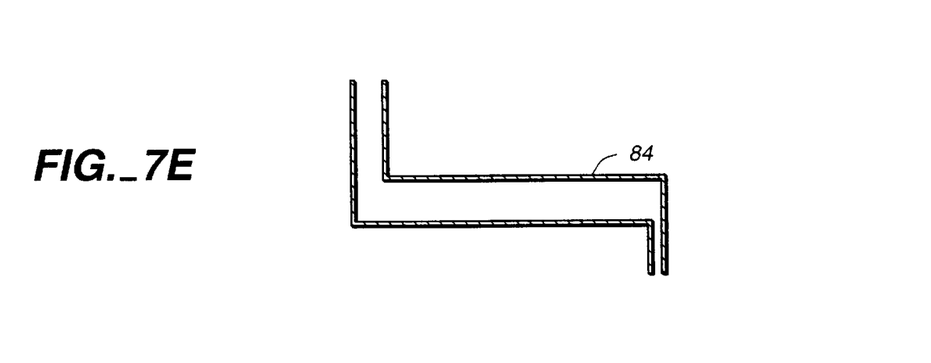

The same process may be used to make enclosed vessels with ports, such as vessel 84 of FIG. 7A, with ports 86, 88 and 90. Such vessels may be used for fluidic devices such as microactuator 104 of FIGS. 8A and 8B. The size of the vessels may be, for example, about 5 microns×5 microns× 100 microns. The ports are formed by providing passages from the mold cavity used to form the body of the vessel to the outside of the mold. The molds 92 and 94 used to fabricate vessel 84 are shown in cross-section in FIG. 7B. The body of vessel 84 is formed using cavity 96 of mold 94. Port 86 is formed using passage 100 of mold 94. Ports 88 and 90 are formed using passage 98 of mold 92 and an additional passage (not shown) of mold 92. The passages may be fabricated using photoelectrochemical etching. Molds 92 and 94 are bonded and coated with a sacrificial layer of silicon dioxide as discussed above in the case of the tubing manifold fabrication. A structural layer 102 of polysilicon is then applied and annealed, as discussed above and shown in FIG. 7C. The polysilicon 102 on the outside of the mold is removed as discussed above and shown in FIG. 7D, leaving behind the polysilicon structure of vessel 84. The vessel is then freed, as shown in FIG. 7E, by etching the sacrificial layer coating the mold.

Figure 8A:
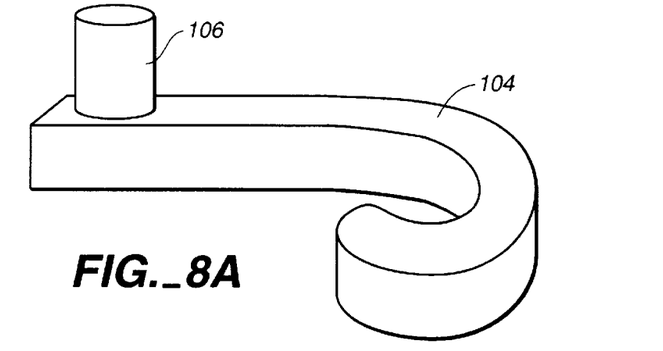
FIGS. 8A and 8B are schematic, perspective views of a hydrostatic actuator or ambient pressure gauge according to the present invention, subject to different pressures.
Figure 8B:
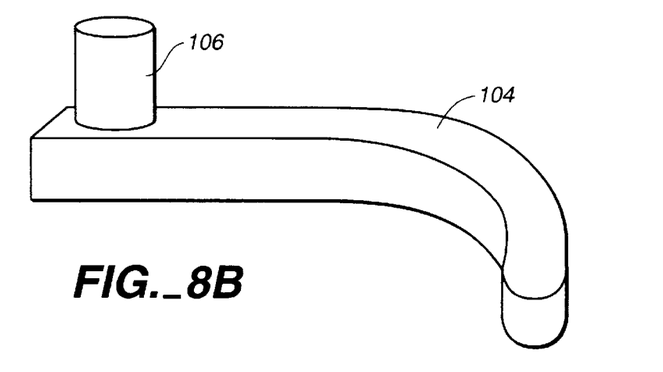

The curved enclosed vessel 104 with one port 106 of FIG. 8A may be used as a hydrostatic actuator or as a Bourdon pressure gauge. When the internal pressure is greater than the external pressure, the curved tube tends to straighten out, as shown in FIG. 8B.

HARMEMS may be integrated with surface silicon applied to the surface of the wafer used as the HARMEMS mold. The term "surface silicon" refers to silicon structures that have a thickness (perpendicular to the wafer they were formed on) on the order of 2 to 6 microns. The resulting structure is a silicon on insulator (SOI) structure. SOI is a silicon wafer on which a layer of silicon dioxide has been formed (typically 1 to several microns thick), and then a second silicon wafer is bonded to this oxide surface. The second wafer is lapped down and polished to leave just a thin layer of single-crystal very large scale integration (VLSI)- quality silicon on the order of 1 to several microns thick, depending on the application. The present invention makes it possible to build an SOI wafer using a HARMEMS mold wafer as the foundation, and then to anchor regains of the SOI wafer to the buried HARMEMS. After the final etch release step, this yields a micromachine carrying microcircuits, unencumbered by a silicon die. This is useful for applications where volume and mass must be minimized.

Figure 9A:
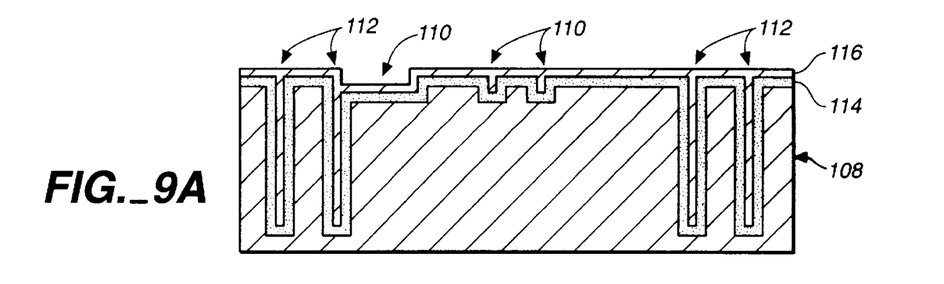
FIGS. 9A–9E are schematic, cross-sectional views illustrating the fabrication of a silicon on insulator (SOI) structure with HARMEMS and surface silicon.

Fabrication of the mold wafer used as the SOI foundation begins with the etching of an alignment pattern on the back of the wafer. This alignment pattern will be used as a reference on a double sided alignment machine for placing the patterns of later mask layers in precise registration with each other. Two microns of LTO are then deposited on the wafer and densified by annealing for 1 hour at 1050° C. The LTO is patterned to provide the etch mask for the surface silicon structures. The silicon of the wafer is plasma etched to a depth equal to the desired thickness of the surface silicon structures plus the thickness of the sacrificial oxide. FIG. 9A shows a wafer 108 with recesses 110 provided as described above.

Trenches 112 (FIG. 9A) for the HARMEMS are fabricated next. Four microns of LTO are deposited and densified as described above. The LTO is patterned to provide a mask for etching the HARMEMS mold trenches 112. The silicon wafer is plasma etched to the depth of the desired HARMEMS plus the desired sacrificial oxide. All the oxide is then removed by HF. As previously described, the wafer may optionally by thermally oxidized and the oxide removed by HF to smoothen the surfaces produced by etching. At this point, the mold wafer is finished, with the final shape shown in FIG. 9A for wafer 108.

A sacrificial PSG layer 114 (FIG. 9A) is then deposited and densified. Next, the structural layer 116 of amorphous LPCVD silicon is deposited and annealed. The wafer is lapped and polished back to the original silicon surface. It is like a new wafer, except that it has mechanical structures buried in it.

Figure 9B:
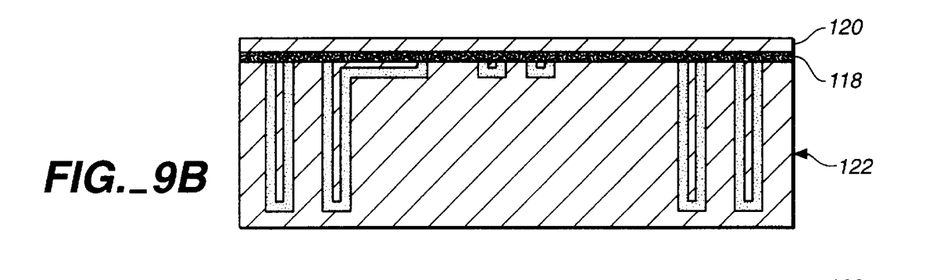

A layer of LPCVD silicon is next deposited and thermally oxidized to yield a layer of silicon dioxide 118 (FIG. 9B). A second silicon wafer (not shown) is bonded to the silicon dioxide surface. This second wafer is lapped and polished down to the desired final thickness for the electronic silicon layer 120. The resulting wafer 122 now looks exactly like a standard SOI wafer and can be processed as such.

Figure 9C:
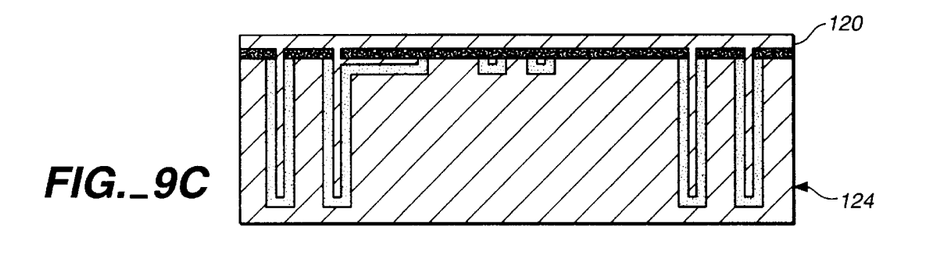
Figure 9D:
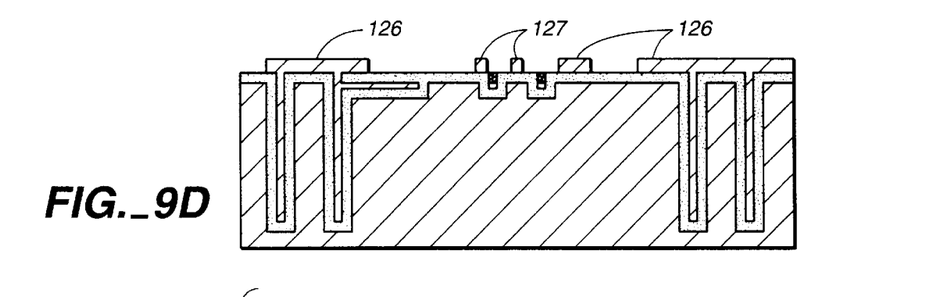
Figure 9E:
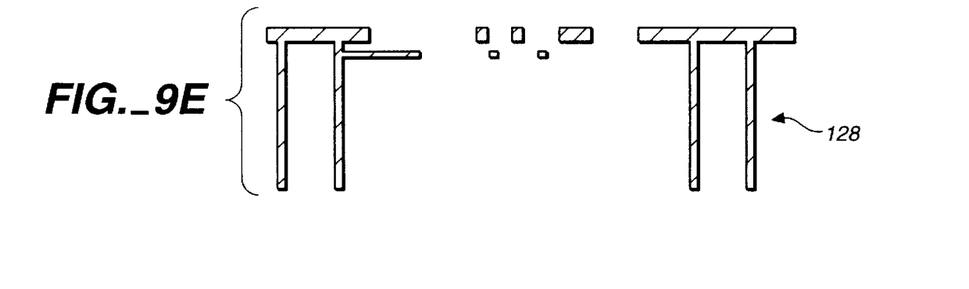

Using the alignment pattern on the back of wafer 122 as a reference, a pattern for anchor contact holes is photolithographically placed on the SOI layer 120. The contact holes are above the buried silicon structures. In the embodiment illustrated in FIGS. 9A–9E, the contact holes would be above trenches 112. The contact holes are etched through the SOI layer and then the oxide layer to expose the surface of the polysilicon of the buried HARMEMS. LPCVD polysilicon is then deposited to fill the contact holes and bond the SOI layer to the buried silicon structures. The surface layer of polysilicon is lapped and polished to leave only the polysilicon in the contact holes and expose the surface of SOI layer 120. The resulting structure 124 is shown in FIG. 9C.

Standard VLSI processing may now be used to fabricate electronic devices in the SOI layer.

The SOI layer 120 is patterned and etched to leave only islands 126 (FIG. 9D) that are located in the desired places on the mechanical structures, including flexible (by virtue of sinusoidal shape) doped conducting interconnects for carrying current between islands 126. The electronic devices (not shown) are covered with a standard silicon nitride passivation layer (now shown), so they are protected from this and subsequent etching processes. The patterning of the SOI layer may also provide a layer of surface silicon type mechanical structures 127 which may interact in cooperation with the surface structures of the polysilicon layer. The completed machine 128 (FIG. 9E) can now be released from the wafer and removed by etching sacrificial layers 114 and 118 as described above.

Figure 10:
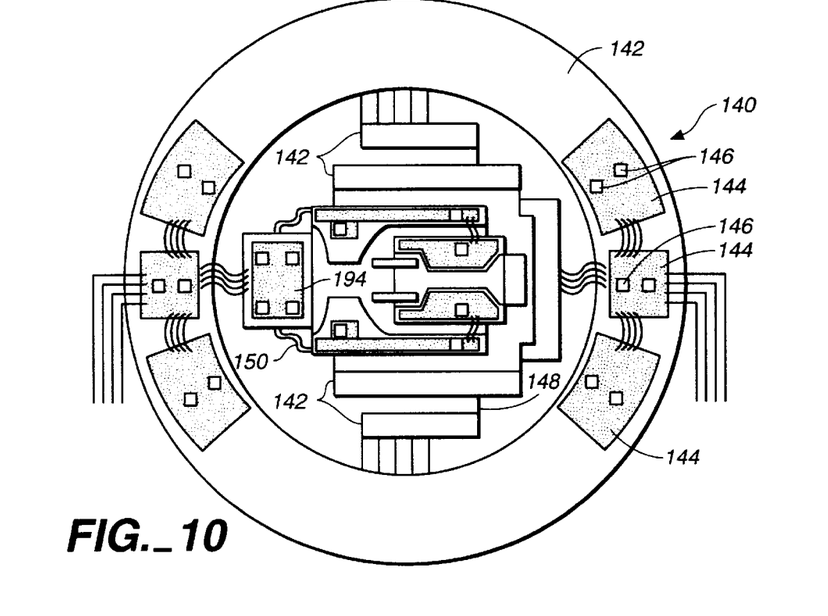
FIG. 10 is a plan view of a machine fabricated using the process of FIGS. 9A–9E.

The design of a machine 140 fabricated using the above process is shown in FIG. 10. The rigid mechanical structures 142 are made of HARMEMS. Overlying some of these structures are layers of single crystal silicon 144, anchored onto the HARMEMS with polysilicon anchors 146. The machine also comprises flexible polysilicon beams 148 and silicon interconnects 150.

Figure 11A:
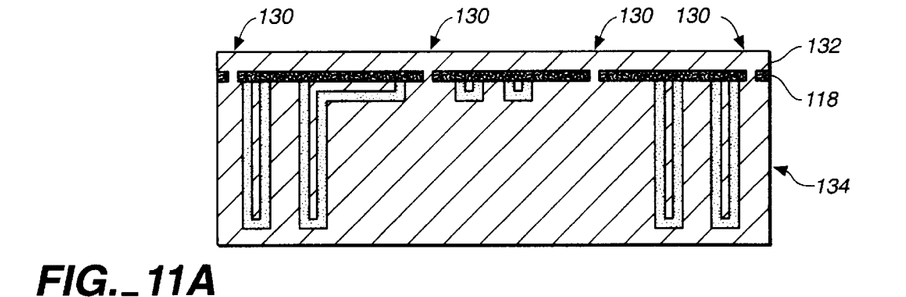
FIGS. 11A and 11B are schematic, cross-sectional views illustrating steps in the fabrication of a SOI structure with HARMEMS and thin film transistor quality recrystallized silicon.
Figure 11B:
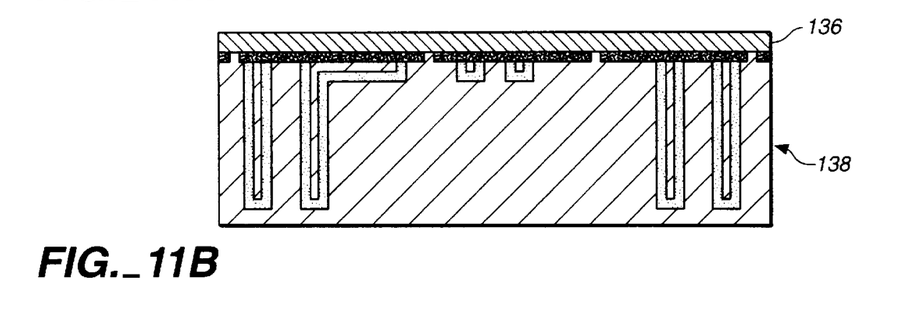

In cases where low performance electronics is adequate, the electronic circuitry layer may be made as described above, but instead of using the SOI strategy to provide VLSI quality silicon, thin film transistor (TFT) quality silicon can be used. As shown in FIG. 10A, the processing sequence is similar to the SOI construction up to the point where the thermal oxide layer 118 is formed. Next, recrystallization windows 130 are etched through layer 118 to expose the surface of the single crystal silicon wafer. LPCVD layer 132 of amorphous polysilicon is deposited next, resulting in the structure 134 of FIG. 11A. The wafer is then annealed at about 600° C. in a recrystallization furnace. The regions of the amorphous silicon 132 that are in contact with the single crystal wafer surface proceed to nucleate the crystallization process, thereby propagating the existing silicon crystal lattice arrangement from the wafer surface up and laterally throughout the LPCVD silicon film. The resulting recrystallized silicon film 136 (FIG. 11B) has too many defects for VLSI circuitry, but it is adequate for many small scale integration (SSI) applications. The resulting structure 138 is similar to structure 122 of FIG. 9B. The subsequent steps are similar to the ones described above for the SOI device case.

Figure 12A:
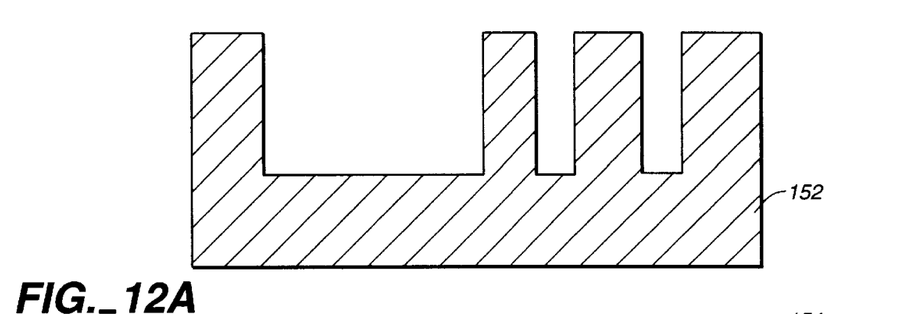
FIGS. 12A–12E are schematic, cross-sectional views illustrating steps in the fabrication of micromechanical structures with very high vertical aspect ratios.
Figure 12B:
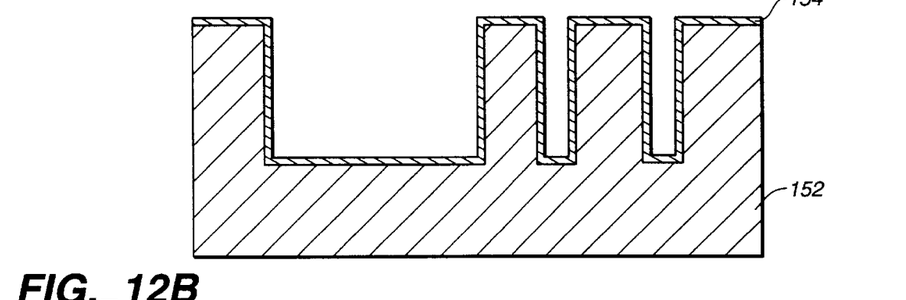
Figure 12C:
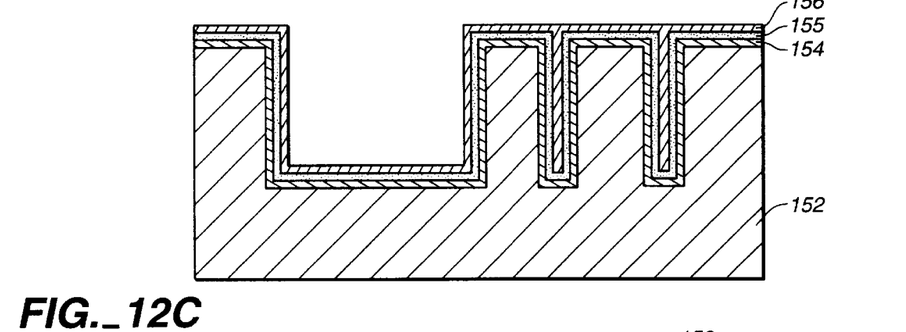
Figure 12D:
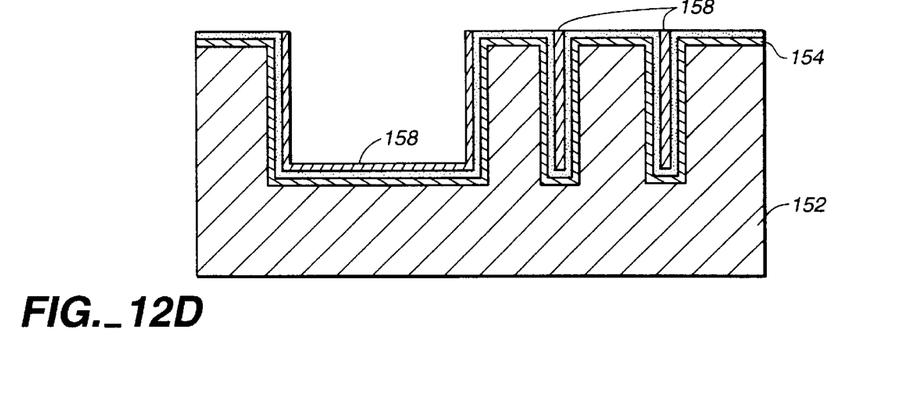
Figure 12E:
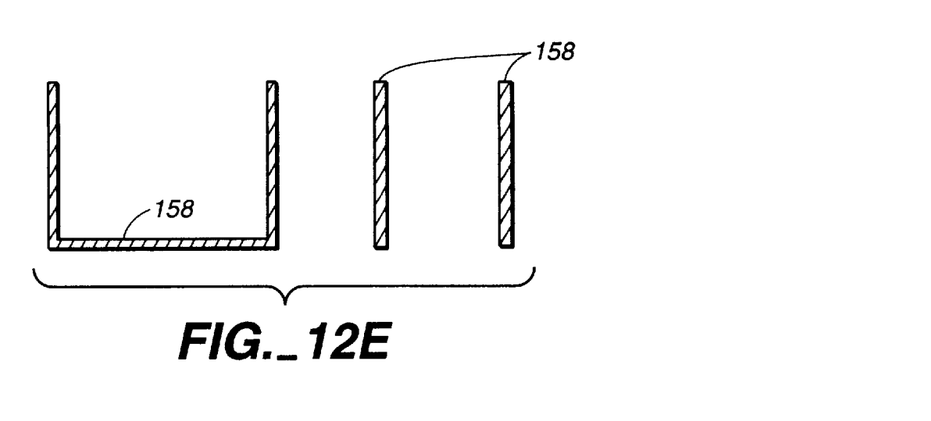

The vertical aspect ratio attainable with anisotropic etching of silicon and PSG sacrificial layers is limited by the unevenness of the PSG layer. Higher vertical aspect ratio structures may be fabricated using a method described with reference to FIGS. 12E–12E. A mold 152 is fabricated as described above. The mold is coated with a layer 154 of CVD polysilicon (FIG. 12B), whose thickness is more constant than that of PSG. Polysilicon 154 is thermally oxidized to obtain a sacrificial layer 155 (FIG. 12C). From this point on, the process is the same as previously described. A structural layer 156 of polysilicon is deposited (FIG. 12C), the surface layer is lapped off (FIG. 12D), and then the polysilicon structures 158 (FIGS. 12D, 12E) are released.

Figure 13:
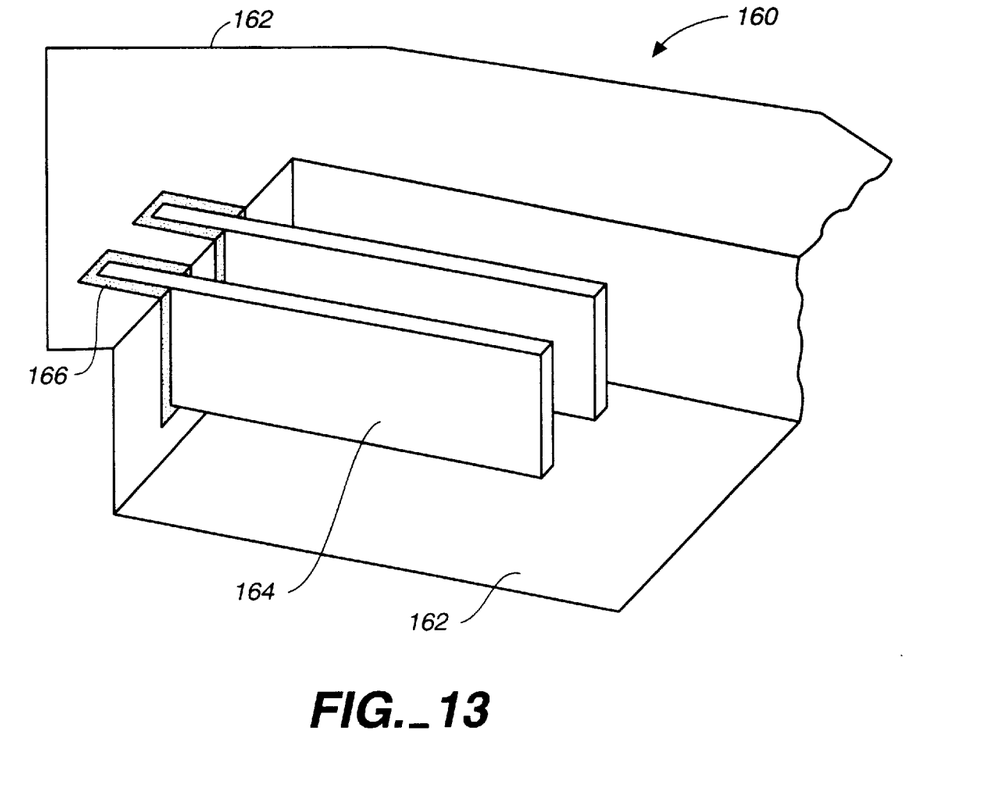
FIG. 13 is a perspective, schematic view of two cantilever beams with large mechanical clearance to wafer.
Figure 14A:
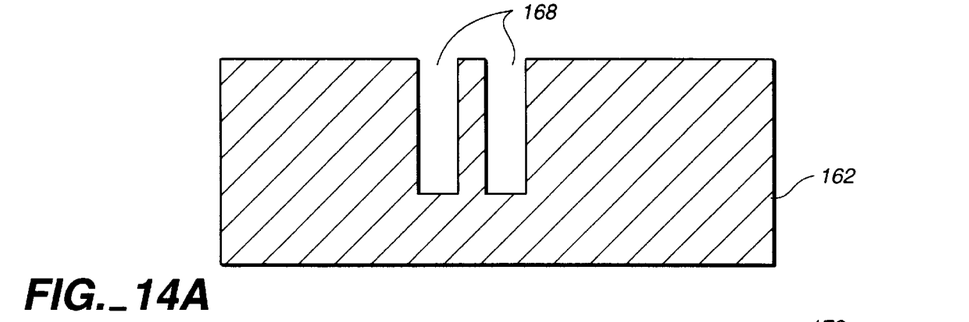
FIGS. 14A–14H are schematic, cross-sectional views illustrating steps in the fabrication of the structure of FIG. 13.
Figure 14B:
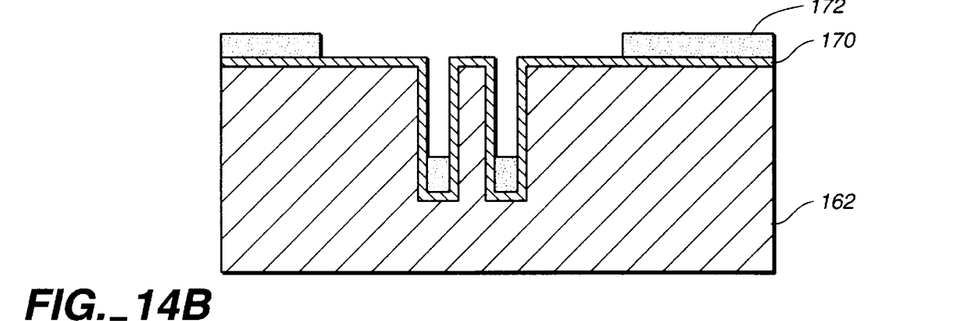
Figure 14C:
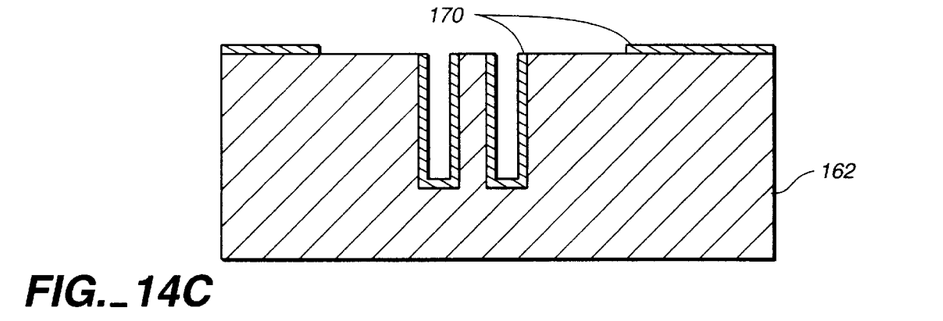
Figure 14D:
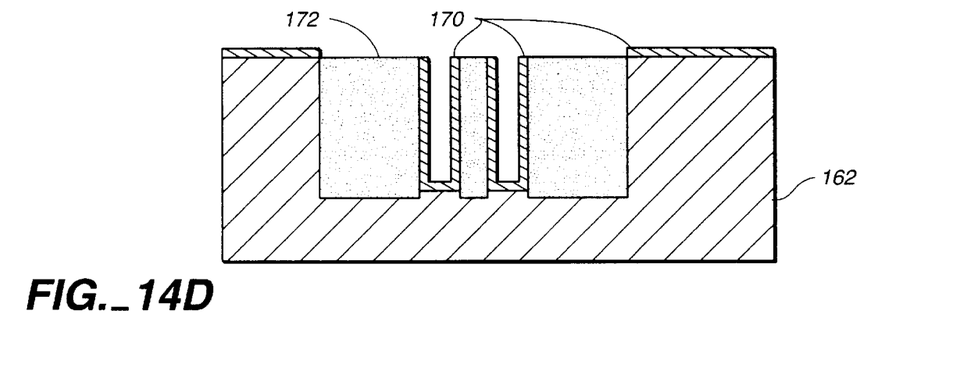
Figure 14E:
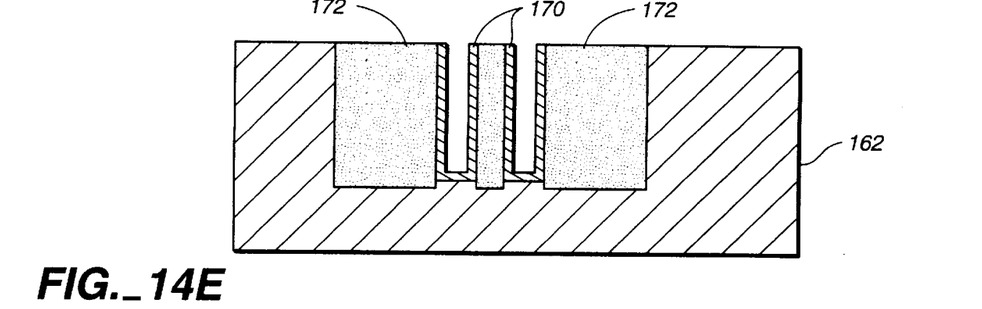
Figure 14F:
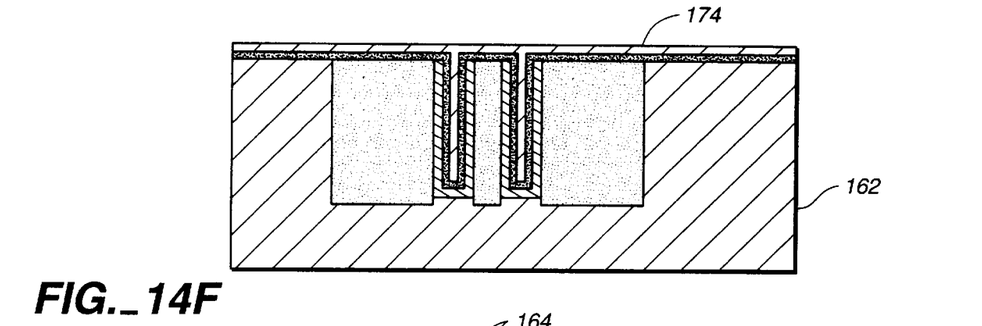
Figure 14G:
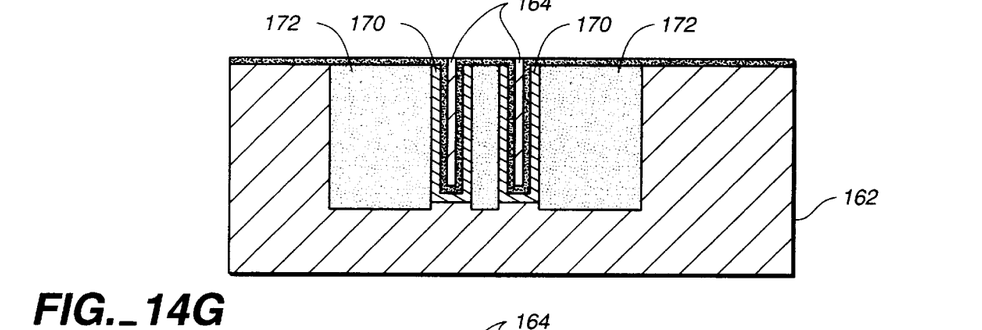
Figure 14H:
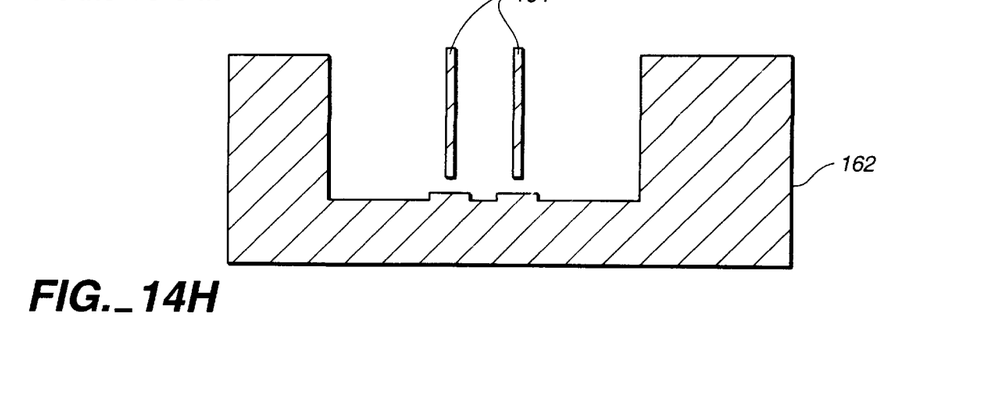

It is also possible to fabricate HARMEMS structures permanently bonded to a wafer and with large final clearance to the wafer. Such a structure 160 is shown in FIG. 13. The structure comprises a substrate 162 and beams 164 anchored to the substrate by anchors 166. Such a structure may be fabricated as described with reference to FIGS. 14A–14D. As shown in FIG. 14A, wafer 162 is first patterned with trenches 168 that serve as molds for the HARMEMS. A bilayer 170 of silicon nitride and polysilicon is then deposited, to serve as a mask for the andization step to follow and as anchors 166. As shown in FIG. 14B, bilayer 170 is patterned using photoresist 171. The bilayer is then etched anisotropically, using $Cl_2$ for the polysilicon and $CF_4$ and $HCF_3$ for the silicon nitride. The resulting structure is shown in FIG. 14C. The silicon wafer 168 is then anodized and the resulting porous silicon oxidized to obtain the structure of FIG. 14D containing silicon dioxide 172. As shown in FIG. 14E, the top portion of bilayer 170 is then removed, for example by lapping and polishing. A structural layer of polysilicon 174 is deposited as shown in FIG. 14F. Its top layer is removed as shown in FIG. 14G. Finally, oxide 172 and bilayer 170 are removed using HF. Anchors 166 (FIG. 13) are masked by the silicon of wafer 162 and not significantly etched.

In summary, high vertical aspect ration thin film structures and methods for their fabrication have been described. Such structures may be used to build fluidic systems and milliscale micromechanical systems.

The present invention has been described in terms of a preferred embodiment. The invention, however, is not limited to the embodiment depicted and described. Rather, the scope of the invention is defined by the appended claims.

What is claimed is:

1. A free standing thin film structure, comprising: a network of ribs each having a thickness and wherein an extent of said thin film structure in any direction is greater than about twice the thickness of any of said ribs.

2. The structure of claim 1 having an extent along said ribs between about 5 microns and about 250 microns.

3. The structure of claim 1 wherein the thickness of said ribs is between about 5 microns and about 15 microns.

4. The structure of claim 1 wherein said ribs form substantially rigid portions connected by substantially flexible links.

5. The structure of claim 4 wherein said substantially rigid portions are networks of said ribs.

6. The structure of claim 5 wherein said networks are honeycomb-shaped.

7. The structure of claim 4 wherein said substantially rigid portions and said substantially flexible links form a machine.

8. The structure of claim 7 wherein said machine is powered by an actuator.

9. The structure of claim 8 wherein said actuator dilates as a result of ohmic heating.

10. The structure of claim 4 wherein said substantially rigid portions further include a planar crystalline silicon part with electronic devices fabricated thereon.

11. An apparatus comprising: a thin film structure having a thickness and an extent, the extent of said thin film structure in any direction greater than about twice said thickness, wherein said thin film structure forms an actuator including a tubular curved vessel having a port whereby pressure may be applied through said port to a fluid in said vessel leading to a straightening of said vessel.

12. A free standing thin film structure, comprising: a honeycomb-shaped network of thin film beams, said beams having a thickness, and wherein an extent of said thin film structure along any dimension thereof is greater than about twice the thickness of any of said beams.

13. The structure of claim 12 wherein the extent of said thin film structure along said beams is between about 5 and 250 microns.

14. The structure of claim 12 wherein the thickness of any of said beams is between about 5 and 15 microns.

* * * * *

UNITED STATES PATENT AND TRADEMARK OFFICE
CERTIFICATE OF CORRECTION

PATENT NO.   : 6,015,599
DATED        : January 18, 2000
INVENTOR(S)  : Keller et al.

It is certified that error appears in the above-identified patent and that said Letters Patent is hereby corrected as shown below:

<u>Title page,</u>
Item [56], References Cited, under U.S. PATENT DOCUMENTS insert:

| | | | |
|---|---|---|---|
| -- 3,936,329 | 2/3/76   | Kendall et al. | 148/187 |
| 3,962,052    | 6/8/76   | Abbas et al.   | 204/129.3 |
| 4,063,271    | 12/13/77 | Bean et al.    | 357/49 |
| 4,307,507    | 12/29/81 | Gray et al.    | 29/580 |
| 4,369,565    | 1/25/83  | Muramatsu      | 29/580 |
| 4,698,900    | 10/13/87 | Esquivel       | 437/52 |
| 4,874,484    | 10/17/89 | Foell et al.   | 204/129.3 |
| 5,126,810    | 6/30/92  | Gotou          | 357/23.6 |
| 5,131,978    | 7/21/92  | O'Neill        | 156/653 |
| 5,262,021    | 11/16/93 | Lehmann et al. | 204/129.55 |
| 5,271,801    | 12/21/93 | Valette        | 156/643 |
| 5,296,408    | 3/22/94  | Wibarg et al.  | 437/203 |
| 5,399,232    | 3/21/95  | Albrecht et al.| 156/633 |
| 5,444,015    | 822/95   | Aitken et al.  | 437/182 -- |

Add: -- FOREIGN PATENT DOCUMENTS
1-138110     5/31/89     Japan --

Add: -- OTHER PUBLICATIONS
W. Lang et al., "Application of Porous Silicon as a Sacrificial Layer," $7^{th}$ International Conference on Solid-State Sensors and Actuators Digest of Technical Papers, June 7-10, 1993, pp. 202-205. --

Signed and Sealed this

Seventh Day of May, 2002

*Attest:*

*Attesting Officer*

JAMES E. ROGAN
*Director of the United States Patent and Trademark Office*